United States Patent [19]

Kaule et al.

[11] 4,381,676

[45] May 3, 1983

[54] APPARATUS FOR SENSING ULTRASONIC WAVES BY OPTICAL MEANS

[75] Inventors: Walter Kaule, Cologne; Erik Primbsch, Ahrensburg, both of Fed. Rep. of Germany

[73] Assignee: Krautkramer-Branson, Incorporated, Stratford, Conn.

[21] Appl. No.: 255,471

[22] Filed: Apr. 20, 1981

[30] Foreign Application Priority Data

May 2, 1980 [DE] Fed. Rep. of Germany ....... 3016879

[51] Int. Cl.³ ..................... G01B 9/02; G01N 29/00
[52] U.S. Cl. ..................................... 73/657; 356/358
[58] Field of Search ................. 73/653, 655, 657; 356/345, 348

[56] References Cited

U.S. PATENT DOCUMENTS 4,013,366  3/1977  Philbert ............................... 356/358
4,046,477  9/1977  Kaule .................................. 356/358
4,129,041 12/1978  Bickel ................................... 73/657

Primary Examiner—Howard A. Birmiel
Attorney, Agent, or Firm—Ervin B. Steinberg; Philip J. Feig

[57] ABSTRACT

An apparatus for sensing the acoustic energy responsive deformation of a workpiece surface by optical means, that is without physical contact with the workpiece surface, comprises the use of a laser light beam illuminating the workpiece surface portion along which the acoustic energy responsive deformation is manifest. The laser light incident upon the workpiece surface is reflected at the workpiece surface and, modulated responsive to the surface deflection, is transmitted to an optical phase interferometer and to a photoelectric means associated therewith. The output from the photoelectric means is transmitted to an evaluation unit. The improvement shown in this invention concerns means for maintaining the reflected light intensity at a predetermined level by comparing the reflected light intensity with a preset level and feeding a control signal to a light control means controlling the laser light intensity incident upon the workpiece surface.

4 Claims, 3 Drawing Figures

APPARATUS FOR SENSING ULTRASONIC WAVES BY OPTICAL MEANS

BRIEF SUMMARY OF THE INVENTION

This invention relates to nondestructive testing of workpieces by ultrasonic energy and more particularly to an apparatus for sensing by optical means ultrasonic waves manifest on the surface of a workpiece, that is, sensing ultrasonic energy without physical contact with the workpiece. Apparatus for practicing this optical sensing method comprise laser means for providing a laser beam which illuminates the workpiece surface portion along which ultrasonic waves are expected to manifest themselves. The incident light reflected at the surface portion, which light is modulated by the surface deflections responsive to the ultrasonic waves, is then analyzed using an optical phase interferometer.

The above indicated arrangement has been described in detail in U.S. Pat. No. 4,046,477 entitled "Interferometric Method and Apparatus for Sensing Surface Deformation of a Workpiece Subjected to Acoustic Energy" of Walter Kaule dated Sept. 6, 1977, the disclosure of which is incorporated herein for reference.

A disadvantage of the prior apparatus resides in the fact that the interferometer sensitivity is influenced by fluctuations of the light measured as caused by changes in the reflection characteristic of the workpiece surface. Such fluctuations may arise, for instance, by the motion of the workpiece surface.

A principal object of this invention, therefore, is the provision of an apparatus which includes means for retaining the light reflected at the workpiece surface substantially constant.

Another important object of this invention is the provision of an apparatus which includes means for controlling the intensity of the light beam striking the workpiece surface as a function of the intensity of the reflected light.

A further object of this invention is the provision of an improved apparatus for sensing ultrasonic waves by optical means when interferometric light analyzing means are used.

Further and other objects of this invention will become more clearly apparent when reading the following description in conjunction with the accompanying drawings.

DETAILED DESCRIPTION OF THE INVENTION

Figure 1:
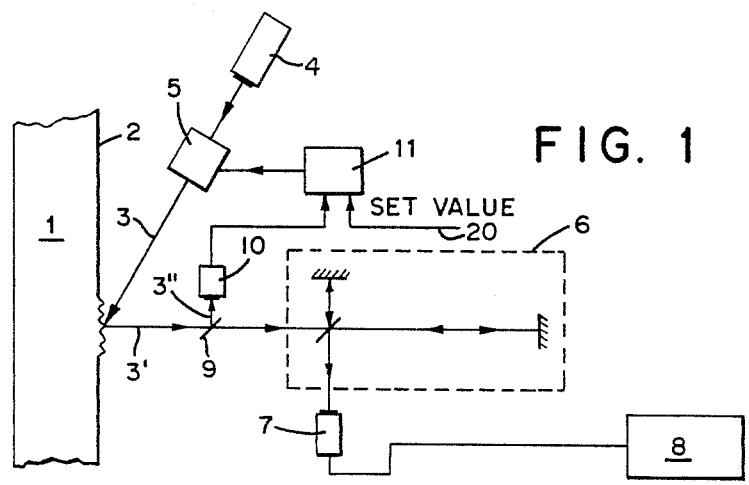
FIG. 1 is a schematic diagram of an embodiment of the invention.

Referring now to the figures and FIG. 1 in particular, there is shown a workpiece 1 having a surface 2 which is illuminated by a laser beam 3 produced by a laser source 4. The intensity of the laser light can be varied by an electro-optical component 5, such as a Pockels cell.

The reflected or scattered light 3' from the surface 2 travels via a phase interferometer 6 to a photoelectric sensing means 7, such as a photoelectric cell. The resulting electrical output signal from the photoelectric sensing means 7 is processed further by an evaluating unit 8.

For the purpose of the present invention an optical beam splitter 9, for instance a partially reflecting glass plate, is disposed in the path of the reflected light 3' in order to adjust the intensity of the light beam 3 incident upon the workpiece surface 2 as a function of the reflected light intensity. The beam splitter 9 reflects a portion of the light beam 3' and provides a signal beam 3" which is a measure of the intensity of the reflected light beam 3'. The signal beam 3" is sensed by a photoelectric sensing means 10 which provides an electrical signal commensurate with intensity of the reflected light beam 3'. An electronic control unit 11, such as a differential amplifier, compares the electrical signal from sensing means 10 with a set value signal 20. If the actual signal value from the sensing means 10 is below the set value signal 20, i.e. the reflected light is of too low an intensity, the intensity of the light beam 3 illuminating the workpiece surface 2 is increased by the control unit 11 providing a suitable control signal to the Pockels cell 5 for adjusting the Kerr cell 5 until the reflected light attains the predetermined intensity. If the signal from the sensing means 10 is above the set signal value, the intensity of the light beam 3 incident upon the surface 2 is reduced until the predetermined intensity is attained.

Figure 2:
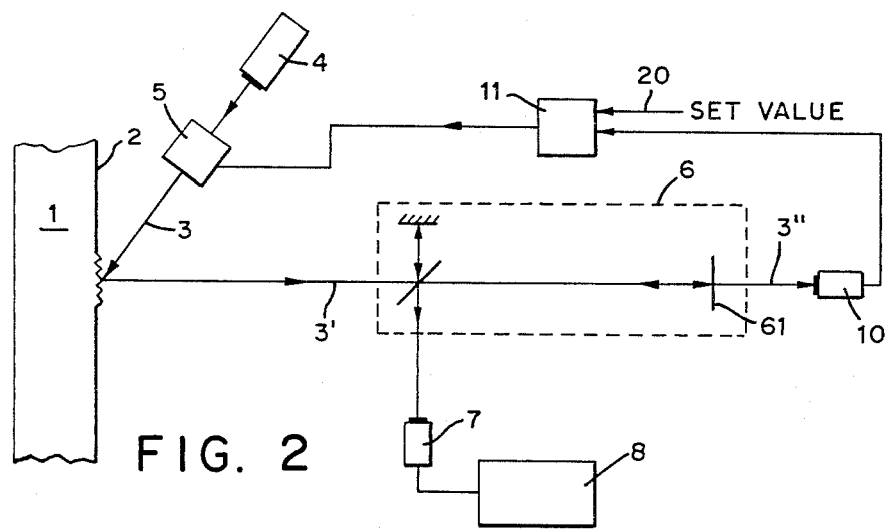
FIG. 2 is a schematic diagram of an alternative embodiment of the invention.
Figure 3:
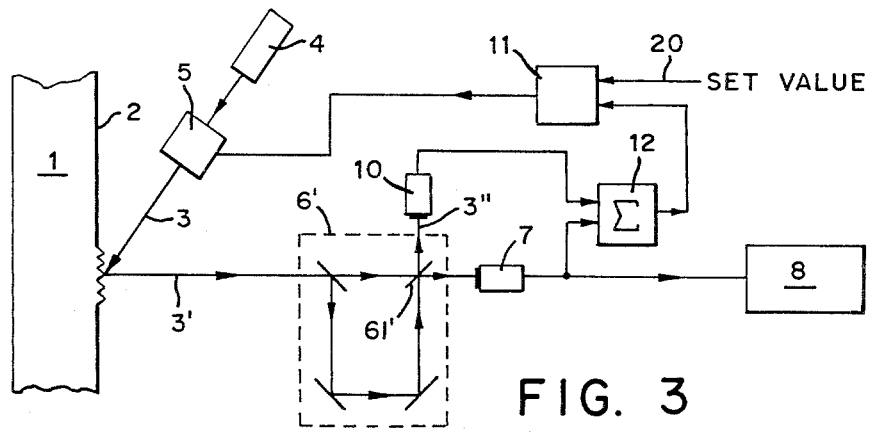
FIG. 3 is a schematic diagram showing a further embodiment of the invention which is particularly suitable for practicing the invention.

FIGS. 2 and 3 depict two other embodiments of this invention in which the need for an additional mirror is obviated, yet the feature of adjusting the illuminating light beam is retained. If a Michelson interferometer 6 is used as shown in FIG. 2, a partially transmitting reflecting mirror 61 is used in one of the two light arms of the interferometer 6. It has been found that the mirror 61 can have a light transmittance of only two percent. The beam portion 3", FIG. 2, once again is a measure of the reflected light intensity and is sensed by a photoelectric means 10. The electrical output of the photoelectric means 10 is transmitted to a control means 11 which receives also a preset value signal 20. As before, the control unit causes adjustment of the Pockels cell 5 to maintain the reflected light at a predetermined intensity.

In FIG. 3 a Mach-Zehnder interferometer 6' having a beam splitting mirror 61' is used. The electrical signals from the photoelectric means 7 and 10 are first supplied to an electrical adder 12 and the adder output signal is coupled to the input of the control means 11 which also receives a signal 20 of predetermined value. Since the optical signals derived from the beam splitting mirror 61' are complementary for the case when the interferometer is properly adjusted, the electrical signal portions related to the sonic signal cancel upon addition. Hence, in contrast with the previously described embodiments, the adder output signal applied to the light intensity control means 5 contains only information related to the fluctuations of the received light without the need to take into account or analyze the fluctuations caused by the ultrasonic wave. This latter system has been found particularly suitable in conjunction with arrangements for sensing ultrasonic waves by the optical means disclosed heretofore.

With regard to a more detailed description of the Mach-Zehnder interferometer, reference is made to Bergmann & Schaefer "Lehrbuch der Experimentalphysik" (book), Vol. III (Optics) 6th edition, Walter de Gruyter, Berlin and New York (1974) page 329.

What is claimed is:

1. An apparatus for sensing by optical interference the deformation of a workpiece surface resulting from acoustic energy present in the workpiece comprising:
   a laser disposed for directing its beam of light upon a surface portion of the workpiece for sensing such deformation, said surface portion reflecting a portion of the incident light;
   light control means disposed for controlling the intensity of the light incident upon said surface portion;
   an optical interferometer disposed for receiving the light reflected at said surface portion;
   first photoelectric means operatively associated with said interferometer for receiving the light from said interferometer and providing a first electrical output signal commensurate with the deformation of the surface portion to an evaluation signal;
   optical beam splitting means cooperatively associated with said interferometer for providing an optical signal which is complementary with respect to the light received by said first photoelectric means;
   second photoelectric means coupled for receiving said optical signal and providing a second electrical output signal commensurate with said complementary optical signal;
   summing means coupled for receiving said first and said second electrical output signal and providing a third electrical output signal commensurate with the sum of said first and second electrical output signals, and
   control means coupled for receiving said third electrical output signal and a set value signal and providing a control signal to said light control means for adjusting said laser beam of light incident upon said workpiece in response to any deviation of said third electrical output signal relative to said set value signal.

2. An apparatus as set forth in claim 1, said light control means comprising a Pockels cell disposed in the path of said beam of light from said laser to the surface portion of the workpiece.

3. An apparatus as set forth in claim 1, said control means comprising a differential amplifier.

4. An apparatus as set forth in claim 1, said optical interferometer being of the Mach-Zehnder type.

UNITED STATES PATENT AND TRADEMARK OFFICE
CERTIFICATE OF CORRECTION

PATENT NO. : 4,381,676

DATED : May 3, 1983

INVENTOR(S) : WALTER KAULE and ERIK PRIMBSCH

It is certified that error appears in the above-identified patent and that said Letters Patent are hereby corrected as shown below:

Column 3, line 17, change "signal" to -- unit --.

Signed and Sealed this

Twenty-third Day of August 1983

[SEAL]

Attest:

GERALD J. MOSSINGHOFF

Attesting Officer       Commissioner of Patents and Trademarks